United States Patent [19]

Furmanski et al.

[11] Patent Number: 4,914,022

[45] Date of Patent: Apr. 3, 1990

[54] METHOD FOR PREPARING MULTIPLE TISSUE SAMPLES FOR MICROSCOPIC INVESTIGATION AND TESTING

[75] Inventors: Philip Furmanski, Littleton; Michael B. Fortuna, Denver; Wen-Hui Wan, Lakewood, all of Colo.

[73] Assignee: AMC Cancer Research Center, Denver, Colo.

[21] Appl. No.: 110,818

[22] Filed: Oct. 21, 1987

[51] Int. Cl.[4] ................ G01N 33/543; G01N 33/552; G01N 33/577
[52] U.S. Cl. ......................................... 435/7; 424/3; 436/518; 436/527; 436/543; 436/548
[58] Field of Search ................... 435/7; 436/518, 527, 436/543, 548; 424/3

[56] References Cited

U.S. PATENT DOCUMENTS 4,820,504  4/1989  Battifora ................................ 424/3

OTHER PUBLICATIONS

Battifora, *Laboratory Investigation*, 55, 244, 1986.

*Primary Examiner*—Sam Rosen
*Assistant Examiner*—David A. Saunders
*Attorney, Agent, or Firm*—Beveridge, DeGrandi & Weilacher

[57] ABSTRACT

A flexible, efficient and rapid method is shown whereby many different tissues samples may be stained or reacted and examined simultaneously, on one standard glass slide. This method is based on the preparation of "cores" of paraffin embedded tissue from standard sources of tissue such as histology blocks. The paraffin embedded tissue cores are inserted into a casing cut from an ordinary drinking straw, or similar holding device, mounted in a paraffin block and sectioned.

8 Claims, 5 Drawing Sheets

METHOD FOR PREPARING MULTIPLE TISSUE SAMPLES FOR MICROSCOPIC INVESTIGATION AND TESTING

INTRODUCTION AND BACKGROUND

Over the past decade, monoclonal antibodies (MoAbs) have come into routine use as essential reagents in clinical and research laboratories and offer great promise for future applications in disease detection, diagnosis, characterization, staging and therapy. See McMichael and Fabre, Monoclonal Antibodies in Clinical Medicine Academic Press, London, N.Y., 1982; St. Groth, Monoclonal antibody production: Principles and practice. In: S. Ferrone and M. P. Dierich (Eds.), Handbook of Monoclonal Antibodies: Applications in Biology and Medicine, Noyes Publications, N.J., p.8.

Much of this value comes from the ability to develop MoAbs with specific or selective reactivity against particular cell or tissue types, developmental lineages or pathologic states (Goding, Monoclonal Antibodies: Principles and Practice Academic Press, London, N.Y., 1983). Irrespective of whether their ultimate application will be as immunohistologic reagents or because of the basic need to establish patterns of reactivity, most candidate MoAbs against cell antigens are necessarily tested against wide arrays of normal and abnormal tissues, usually by immunohistochemical methods. This process is extremely tedious, time consuming, labor intensive and costly in terms of reagents and tissue samples.

Recently there has been described a method for combining multiple tissue samples into a single "sausage" composite held together with a wrapper of intestinal casing. The tissue samples are obtained from deparaffinized histologic blocks. The multiple tissue sausages are reembedded in paraffin, sectioned and mounted on slides to screen and characterize candidate MoAbs. Using this procedure, a hundred or more tissue samples can be tested simultaneously with a single antibody preparation on a single slide. See Battifora (1986), The multitumor (sausage) tissue block: Novel method for immunohistochemical antibody testing. Lab. Invest. 55, 244, 1985.

While this innovative approach is useful and efficient, it also has a number of inherent difficulties and disadvantages. Preeminent among these drawbacks is the need to deparaffinize and reembed tissue samples, which could lead to further loss of antigens of interest time and technical effort required to prepare the sausage composites; problems in maintaining spatial relationships among the pliable tissue samples in the sausages, complicating the scoring of reactivity; and a lack of ease and flexibility in choosing the tissue samples for and preparation of the sausages, particularly with small specimens.

SUMMARY OF THE INVENTION

There has now been developed a new procedure which alleviates these problems of the known sausage technique. In the method of the present invention tissue "cores" are bored from tissue samples, such as standard paraffin blocks, and directly assembled in plastic straws to form rigid, spatially-fixed, multiple tissue plugs that can be sectioned and stained using routine procedures. Virtually any paraffin embedded tissue can be cored; deparaffinization and reembedding are not required. Small specimens are as easily handled as large samples. Straws containing multiple tissues can be rapidly assembled from libraries of cores or paraffin blocks in any combination desired. The samples may include specific regions of interest from individual sections or blocks. These multi-tissue straws can be used to rapidly and efficiently screen and characterize candidate MoAbs.

It is accordingly an object of the present invention to provide a method for simultaneous histologic testing of multiple (e.g. 24 to over 240) individual tissue specimens on a single slide. The method is applicable for rapid and efficient testing of tissue reactions with any of a variety of staining reagents. The method is highly suited for screening, selection, and characterization of candidate monoclonal antibodies, which usually require testing of the antibodies against many normal and pathologic tissue samples to discern patterns of reaction and, hence, utility. Therefore, the present invention avoids the problems of prior methods which required each tissue sample to be individually sectioned and mounted on a single slide. The highly time-consuming, labor-intensive and expensive process of the past are accordingly rendered obsolete.

A further object of the present invention is to provide a method that can be used to test and verify new chemical or biological stains, substrates for enzymes, histochemistry, genetic probes, and other reagents which are designed to be applied to tissue sections. In addition, the method is applicable to sections of animal or plant tissues, microorganisms or particulates (embedded as pellets or suspensions). Multitissue slides prepared using this method may also be used to provide the "control" samples in commercial immunohistochemical or cytochemical test kits.

In attaining these and other objectives, one feature of the invention involves preparation of small "cores" of tissue samples from routine paraffin embedded tissue blocks. Other sources of samples such as frozen tissue can also be used. The cores of numerous tissues of interest are combined, infiltrated with paraffin, remounted into a single block and sectioned. A single section, and hence one slide, may thus contain any assortment of tissues required for analysis.

Advantages of the present invention include greatly enhanced efficiency and speed for tissue testing; greatly decreased cost for multiple tissue testing; great economies in the use of tissue samples, reagents and test materials such as antibodies; great flexibility and ease of constructing multitissue samples of interest; greatly increased ease in scoring tissue reactivities; ability to combine screening and characterization selection of reagents of interest; ability to select regions of interest for testing from heterogeneous tissue samples.

Additional advantages of the present invention, especially with regard to the previous multitissue sample preparation method include: greatly increased ease of preparation; greatly increased speed of preparation; greater flexibility in sample assortment; lack of need for deparaffinization, reembedding and heating of tissues, which could lead to loss of reactivity; lack of need for specifically sized or shaped tissue samples; retention of spatial relationships among samples in the multitissue "straw", resulting in greater ease in carrying out reactions and scoring them; stability of individual tissue "cores".

In its broadest aspects the present invention relates to a method for preparing tissue specimens for investigation of a wide ranging nature including evaluation, testing or controlling any microscopical staining or marking procedures. It has particular importance and relevance for testing immunohistochemical reactivity of monoclonal antibodies against multiple tissue samples simultaneously. In further detail, the method of the invention resides in providing a plurality of tissue specimens of any type, animal or human, tumorous or non tumorous, and "coring" each of the tissue specimens to obtain a plurality of core specimens. The cores are then assembled in a holding device which can be a hollow, cylindrically shaped paper or plastic tube. The assembly of cores in the tubular holder is then fixed in position by embedding the assembly with a suitable binder matrix which can be natural or synthetic, polymeric or non-polymeric material, preferably paraffin or other wax substance. The result is the formation of a physical block of a plurality of tissue specimens which can then be sliced into a sections for investigation, testing and/or control according to the desired microscopic procedure.

BRIEF DESCRIPTION OF THE DRAWINGS

The invention will be further understood with reference to the drawings wherein:

FIGS. 1A to 1F show the steps in the preparation of multiple tissue core straws; to wit.

FIGS. 3A and B show examples of immunoperoxidase stained cores.

DETAILED DESCRIPTION OF THE INVENTION

The starting materials for preparation of tissue cores can be any convenient source such as routine paraffin blocks, frozen tissue and the like. The technology involved in preparing paraffin blocks is well understood and described in the art. It has been found that both freshly prepared blocks and those stored for periods as long as 20 years may be successfully cored—their utility dictated only by preservation of morphology and antigens of interest (if the samples are to be used for immunohistochemistry). Generally, blocks containing tissue samples 0.5 to 1 cm thick are the most useful since the resulting multi-tissue straws which they are used to construct will yield significant numbers of sections for slides. However, embedded tissue slices as thin as 0.5–1 mm have been used and, where feasible, thick samples of small or thin tissues have been prepared by stacking the pieces within a block. If desired, sections may be taken from the parent tissue paraffin block prior to coring, stained and used to localize particular structures of interest to be included in the cores. This is described in further detail below under the "Results".

Figure 1A:
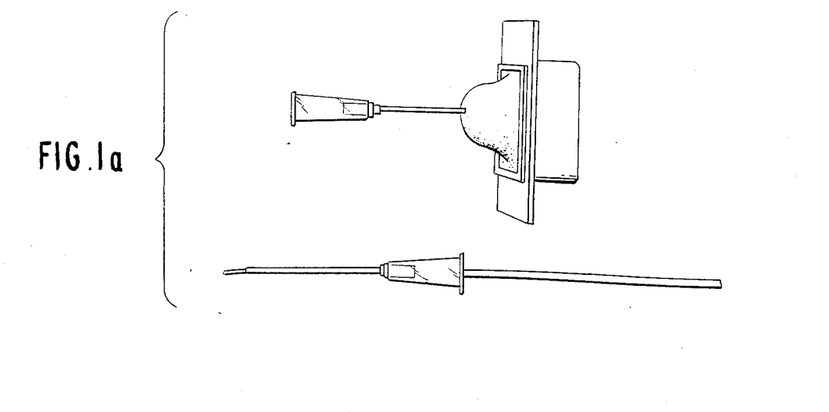
FIG. 1A shows a modified needle and matching stylet used for coring and core extrusion and a paraffin tissue block being cored.

The cores of embedded tissue are manually bored from the tissue blocks using a 16 gauge syringe needle from which the point has been removed and the edge bevel sharpened using a fine grit sharpening stone. An example of this device is shown in FIG. 1A. The upper device shows the coring needle boring into a paraffin block of tissue shown mounted in a conventional holder mount of the type used in any laboratory microtome. A handle, not shown, (for example, the barrel of a syringe) is normally added to facilitate holding the boring tool. The resulting tool resembles a miniature cork borer. Any suitable boring device may be used. This step can be performed manually, as stated, with a single tool; or the boring process could also be conducted with a suitable electronically controlled boring or core machine to cut a plurality of cores simultaneously or sequentially. The dimensions of the "coring" or boring device can vary as will be apparent to those skilled in the art.

Mounted in a comfortably sized barrel of a plastic syringe (usually 10 or 20 cc, without the plunger), tissue cores can be removed from the original paraffin blocks using the sharpened and beveled needle with no more than moderate hand pressure and, if necessary, a slight twisting motion. After the needle has been pushed through the paraffin block and then pulled out of it, the tissue cores are extruded from the needle using a snugly fitting wire stylet as shown in the lower device in FIG. 1A. Any suitable "pushing" tool can be used to remove the tissue core from the hollow needle boring device. It has been noted that manner of the tissue cores thus produced assume a slightly bowed or curved shape. The resulting tissue cores are typically curved in shape. After straightening as described below, the cores may then be assembled together into multi-tissue assembly holding device, such as a drinking straw, as described below or stored in vials indefinitely as a part of a library. See FIG. 1C.

Preparation of multi-tissue "straws"

Cores of tissues selected for inclusion in a multi-tissue straw are freshly drawn from a library of paraffin blocks or frozen tissue, or a library of previously obtained cores, and ordered in the fashion desired. A "marker" core with a distinguishable pattern of staining or an easily recognizable tissue or structure is typically included for orientation. This is simply any easily recognized or distinctive core (containing a particular tissue or other marker) placed at one particular location in the multitissue straw to aid in orientation when examining stained sections.

Figure 1B:
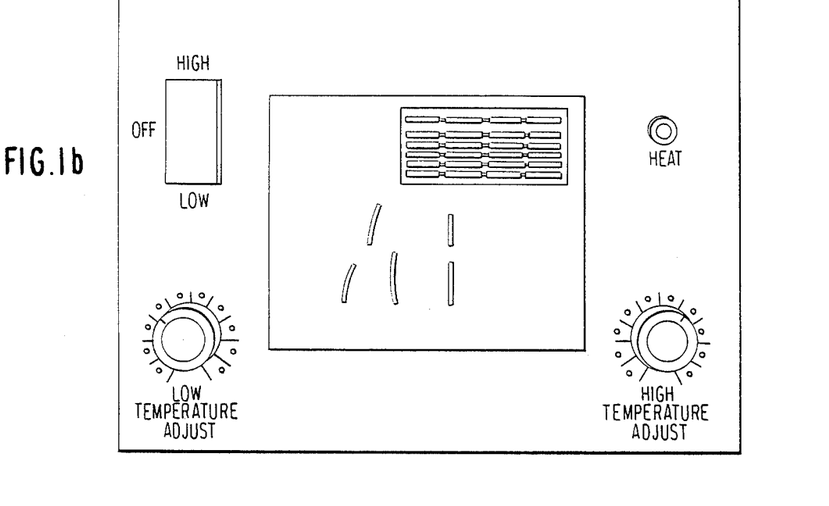
FIG. 1B shows straightening of extruded cores on a heating block and use of a grooved aluminum plate for holding the straightened cores in sequence.
Figure 1C:
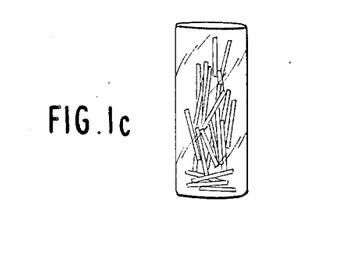
FIG. 1C shows paraffin tissue cores stored for use.
Figure 1D:
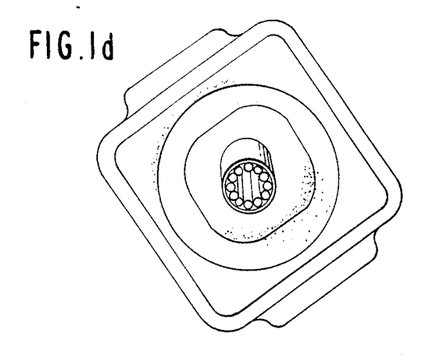
FIG. 1D shows a straw partially filled with tissue cores.

If the cores are curved in shape as a result of the boring operation, they are then straightened by softening and then gently rolling them with a fingertip on the solid surface of a thermostated heating block or slide warmer maintained at 40°–45° C. This is shown in FIG. 1B. When preparing large numbers of straws, the cores may be straightened on the heating block and placed on an aluminum plate (6.3 mm thick) lightly grooved to hold them in place and in order. Cores that break or split may be "glued" together using the heat of the block. The pliant cores are very briefly cooled in air to regain rigidity and are then placed directly into a casing consisting of an ordinary plastic drinking straw (6.3 mm diameter) cut to a length matching the length of the tissue core samples used. This is shown in FIG. 1D.

Figure 1E:
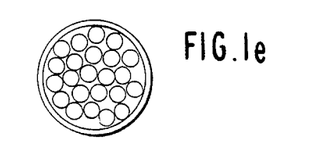
FIG. 1E shows finished straw assembly with drinking straw casing not yet removed.

With the plane of the opening perpendicular to the heated surface, the cores are each precisely aligned in the straw using forceps or a stylet and, using the heat of the thermostated block, lightly adhered to the inner surface of the straw and/or adjacent cores. In this way, straws are typically filled with a plurality of, e.g. 24 (or more) selected tissue cores as shown in FIG. 1E.

The straws must be filled with a sufficient number of cores so that the cores are held in the straw by slight pressure, but not so many that the force of getting the cores into the straw or the pressures within the straw distort the tissues. In addition, the cores are usually aligned in the straw in concentric circles, and it is easier to do so by filling each circle completely, with the cores held in place, again, by slight pressure against each other, much as using a keystone in constructing arches or circles. Using standard plastic drinking straws and the size cores specified, it has been found that the number of cores per straw that satisfies these criteria is 20–28, with 24 a good average, but of course other size/number combinations are also possible. It is convenient to use a standard number of cores per straw for planning core preparation and examining stained tissue sections. The completed straw is then placed upright into a suitable holding means, such as an embedding base mold containing a drop of molten paraffin, wax, or other suitable inert thermoplastic material that is nonreactive with the core, and held for further processing.

Paraffin was used, as this is the standard embedding material for fixed, permanent histologic or pathologic tissue sections. However, any other "binding" material could have been used, including binders used for frozen sections, epoxies used for ultrathin sections, and the like.

In an alternative method for filling the straws with tissue cores a drop of molten paraffin, or equivalent material, is first put in an embedding base mold. The mold is placed on the heating block to maintain its softened consistency. A segment of cut plastic straw is positioned upright in the paraffin so that its opening is parallel to the heated surface. The previously prepared cores are then gently inserted into the straw casing.

Figure 1F:
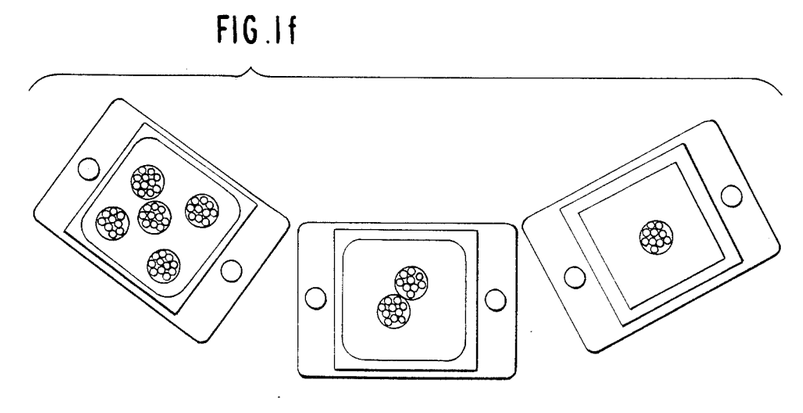
FIG. 1F shows finished assembly of tissue specimens with drinking straw casing removed embedded in paraffin blocks, configuration of one, two and five straws per block which are ready for sectioning.

Additional paraffin is then added to the strawcontaining embedding molds, which are then placed into a 60° vacuum oven under 15–20 pounds negative pressure for 15 minutes. The molds are removed from the oven, cooled, and the paraffin block detached Excess paraffin is trimmed from the straw using a scalpel or other convenient removal means. Thereafter, the straw casing is removed, leaving behind a solid paraffin plug containing the multiple tissue cores, which are then embedded in a paraffin block as shown in FIG. 1F.

As required, one or more multiple tissue straws, or segments cut from them, may be embedded in a paraffin block and sectioned. If not immediately needed, the paraffin plugs may be stored indefinitely under suitable conditions.

Immunoperoxidase staining

To illustrate the utility of the method, tissue sections and multi-tissue straws were immunohistochemically stained using the Vectastain ABC kit (Vector Labs, Burlingame, CA). Monoclonal antibodies used included ones developed in the laboratory of AMC Cancer Research Center, Denver, Colo., in the course of studies on the expression of differentiation antigens in breast tumors. It will be apparent that any suitable monoclonal antibody or conventional morphologic, immunohistochemical, cytochemical or enzymatic staining procedure can be used in accordance with the present invention.

Results

The basic steps of this procedure are illustrated in FIG. 1, A–F. The cores are easily prepared and handled, with little chance of harm or deterioration. The temperature of the heating block is adjusted to the facility of the operator in softening and straightening the cores without melting the paraffin. The exact temperature is therefore not critical, provided excessive temperature that would damage the specimens is avoided. After brief air cooling, the rigidity of the cores enables their precise alignment in the straw, a great help in constructing the multi-tissue specimens and in maintaining the desired orientation and spatial relationships among the tissue cores.

Figure 2A:
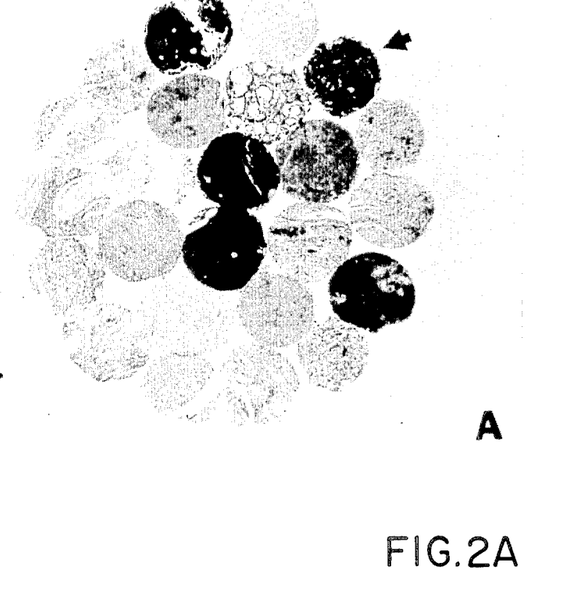
FIG. 2A shows representative example of a hematoxylin-eosin stained multiple tissue straw containing cores of various normal human organs (X 3.125)

FIG. 2A shows a low power magnification of a section of a straw containing a variety of human tissues.

Figure 2B:
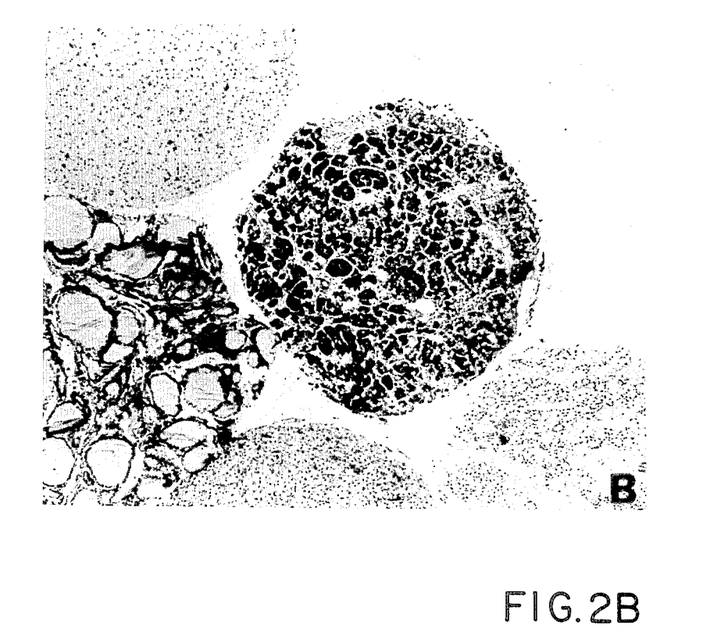
FIG. 2B shows a higher magnification of a core (human pancreas) contained within the straw in FIG. 2A (arrow) demonstrating the retention of structural integrity (X 12.5)

FIG. 2B shows a higher power view of one of the cores, demonstrating its uniformity and retention of morphological integrity.

Figure 3A:
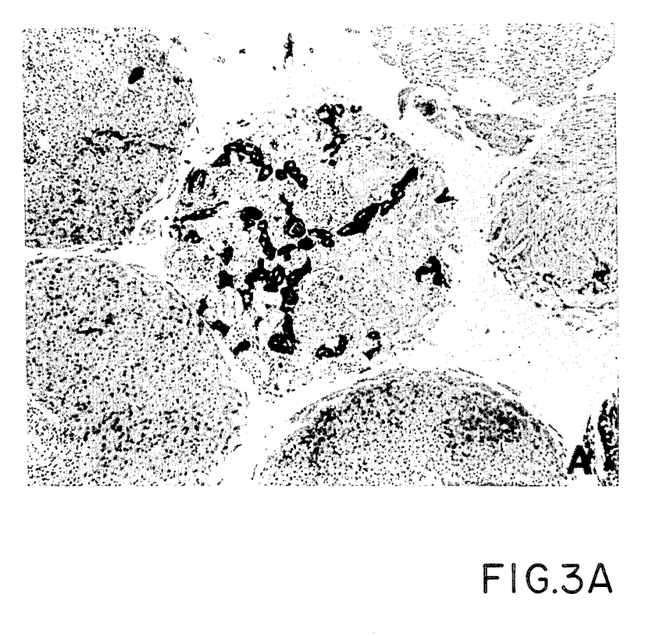
FIG. 3A is a normal human kidney core stained with MoAb MR13.B10 counterstained with hematoxylin (X 12.5). The absence of staining in surrounding cores of tissues from other normal human organs is to be noted.
Figure 3B:
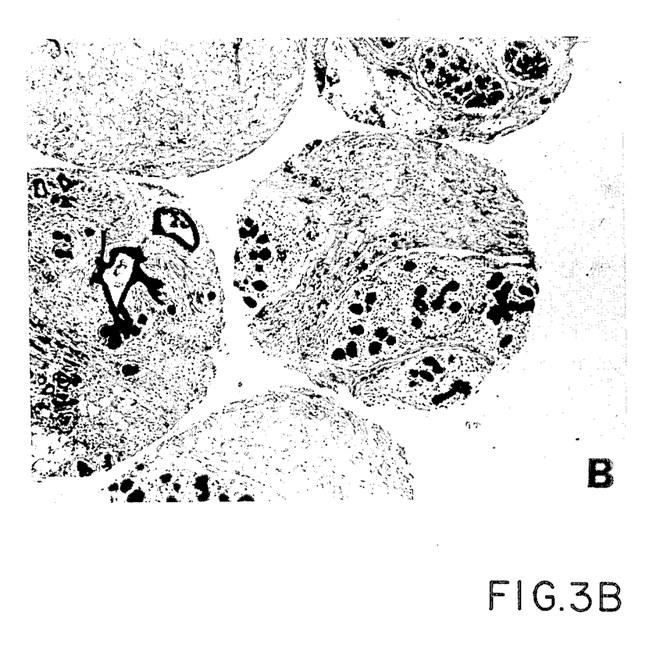
FIG. 3B shows a straw containing normal human breast tissue cores stained with MoAb LB1.D counterstained with hematoxylin (X 12.5). The localized staining of ductal epithelial cells in the cores containing these structures is to be noted.

Many different human and animal tissues, both normal and abnormal, have been cored without any deleterious effects, such as disintegration, tearing or compression. Immunoperoxidase staining of individual tissue cores with various MoAb's is qualitatively and quantitatively the same as staining on the tissue sections from which they were derived. Examples of MoAb immunoperoxidase staining of tissue cores are shown in FIGS. 3A and 3B.

Figure 4A:
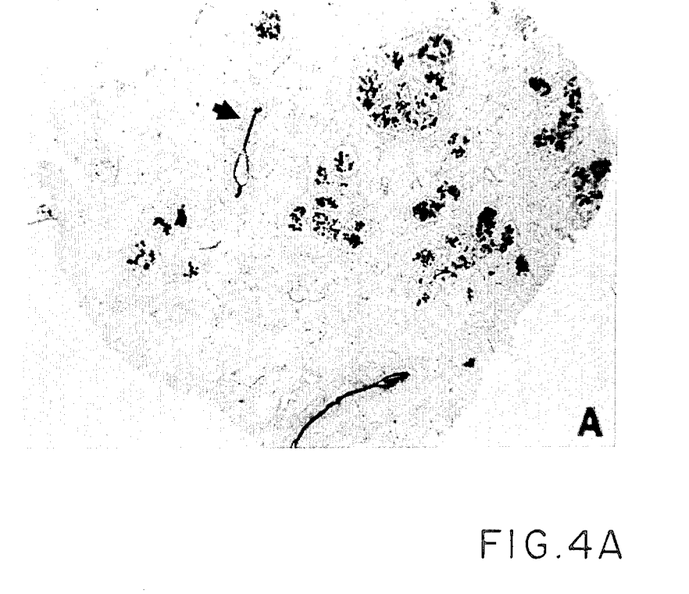
FIG. 4A shows traditional full paraffin section of normal human breast tissue stained with hematoxylin-eosin (X 3.125). The structure identified by the arrow was selected and purposefully cored for inclusion in the straw of FIG. 4B (inverted), also stained with hematoxylin-eosin (X 16.5).
Figure 4B:
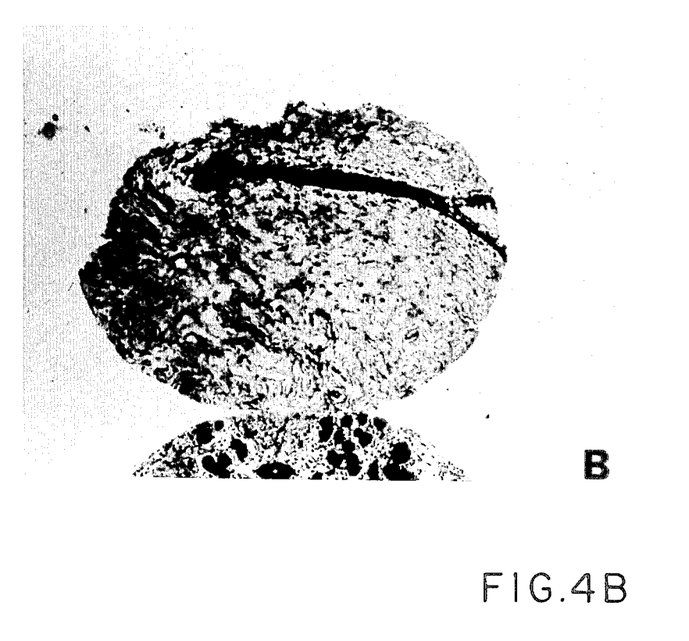

Individual structures or isolated areas of interest may be identified from a traditional tissue section for inclusion in a core. An example is shown in FIG. 4A and 4B, in which a section was taken from a block of normal human breast tissue, a structure or region of "interest" was identified, and the identified area cored with the inclusion of the structure in sections of the core.

With only a little practice, an operator can select the needed tissues from a "library" of cores, straighten them and fill a straw or other suitable assembly holding device with them in less than 15 minutes. Infiltration, trimming, mounting in a block, and sectioning, can be achieved within an hour. Blocks containing as many as 5 straws, or a total of 120 distinct tissue samples, are routinely prepared and used to screen and characterize MoAb's (FIG. 1F); inclusion of more cores per straw or more straws per slide is quite feasible.

Sections with 5 straws (containing a total of 120 cores) on a single slide can be fully saturated with 250 μl of diluted primary antibody. A section of a single straw containing 24 cores can be circled with a grease pencil or PAP pen (Daido Sangyo Co., Japan) and covered with as little as 75 μl of diluted antiserum or tissue culture fluid.

One of the approaches most frequently used in the selection and characterization of MoAbs for clinical or experimental applications is the determination of their immunohistochemical reactivity against panels of normal and abnormal tissues. This has traditionally required the preparation and staining of large numbers of routine histologic sections, at a considerable cost in time, specimens, reagents and antibodies. Laboratories engaged in monoclonal antibody development have often substituted ELISA or radio immunodetection systems performed by automated or semi-automated equipment. However, where antibodies are sought that are reactive against uncommon structural components, individual cells in mixed populations or other morphologically defined components, immunohistochemistry must still be carried out, often even at the initial screening stages where large numbers of candidate hybridoma colonies need be tested.

The use of stable, semirigid paraffin cores enables rapid assembly of any combination and permutation of tissue samples of interest for immunohistochemical tests. The ability to combine straws, or slices of straws, into a single block, provides an additional level of flexibility. For the work reported here, a library of cores of a variety of normal and abnormal tissues is maintained, as are standard straws of a wide array of different normal tissues, straws of an array of abnormal tissues, and straws containing cores of normal, benign and malignant specimens of a single histotype; from this library, straws can be quickly constructed and/or combined to produce sections containing tissues relevant to the screening and characterization of any particular set of candidate MoAbs. The time from selection of tissues for testing from a "library" of blocks or cores to the sectioning of completed and embedded straws can be as little as one hour. One hundred and twenty tissue samples, or more, can be routinely tested on a single slide with 250 μl of diluted antibody.

The uniformity of core size enables rapid initial review of MoAb reactivity. The fixed spatial relationships among the cores in a straw allow accurate tissue identification and scoring even by untrained observers using "maps" of sample orientation. The coring procedure allows the sampling of discrete, even minute, regions of interest directly from the paraffin block. Morphologic integrity and antigenic reactivity, relative to sections of the parent paraffin block, are fully retained in the cores.

The sizes of the individual cores and straws may be readily altered, although it has been found that those described here easiest to work with. Cores prepared with a 16 gauge needle contain a sufficient number of cells to represent an adequate sampling of most tissues, yet are small enough to be easily bored from paraffin blocks and readily manipulated, and are materially conservative. In addition, the sections of this diameter core are contained within the field of view under a 10X objective, a convenience when scoring. The size of an ordinary drinking straw, used as a casing for the multiple tissue cores, is also convenient as it is viewed in its entirety under a 2.5X objective. Although up to 32 cores have been placed into a straw, 24 cores per straw has, in our experience, proven to be a reasonable and easily achieved working number. More samples per slide can be conveniently and flexibly included by using multiple straws per block.

Although the small size of the cores may promote sampling errors due to tissue heterogeneity, this concern is more apparent than real, as it might be applied to any individual section taken from a piece of a tissue specimen. Indeed, if of concern, multiple core samples of a single tissue, either taken randomly or preselected from a stained section of the block, can be included in a straw.

Any cylindrical material could have been used to hold the cores. The only requirements are that the holding device be made of material that is not soluble in paraffin (or any other embedding material employed), be resistant to the brief heating used to infiltrate the straw with embedding material (when used—60° C. for 15 minutes, irrelevant in the case of frozen tissue embedding material), and be easily remolded after infiltration (plastic or paper) or easily sectioned if left on.

The preferred shape is cylindrical, but conceivably one could use holding devices with any shaped cross section; e.g. square, rectangle, polygonal.

The dimensions used were chosen for convenience in preparation and microscopic examination. That the cores are fully visualized under the 10X objective, and the entire straw visualized under the 2.5X objective, makes it somewhat more convenient when scoring reactions with the microscope. These sizes are also easily handled and conservative of materials. Use of smaller numbers of cores in smaller straws would probably not be efficient. However, larger sizes can be used, limited only by application and practical considerations of tissue sample size and handling. Generally, for example, pathologic specimens are less than 1 cubic centimeter because fixation and infiltration are much poorer in larger specimens. Therefore, the length of samples, and hence the length of the cores and straws, will usually be limited by convenience to about 1 cm (although tissues can be stacked to make longer cores). Longer ones also are more difficult to handle and align and commit too much tissue to any single block. By the same token, there are microtomes that will section blocks several inches on a side, so that one could conceivably prepare a 1 cm thick "straw" 3 inches or so in diameter holding thousands of cores.

The surface to which the cores are applied is typically a 1"×3" microscope slide, although this is not a requirement and there are other sizes of slides that may also be used. Glass slides were used because the method is developed for microscopy, which uses glass slides almost exclusively. The surface of the slide must be scrupulously clean and is often precoated with gelatin or albumin to facilitate adhesion of the sections. This is standard practice for immunohistochemical staining procedures on any type of sample.

Further variations and modifications of the foregoing invention will be apparent to those skilled in the art and are intended to be encompassed by the claims appended hereto.

The work reported herein was supported by grant CA 43174 from the NIH.

We claim:

1. A method for preparing multiple tissue samples for investigation and testing, comprising:

providing a plurality of tissue specimens, boring at least one core from each of said tissue specimens, assembling a plurality of cores of said tissue specimens in a suitable preformed holder, whereby said cores retain the same spatial relationship throughout the length of the holder immersing said holder containing said plurality of cores in a heat softened synthetic or natural binder matrix and solidifing said binder matrix, removing said holder without disturbing said plurality of cores, cutting at least one section of said assembly of cores in a sufficient thickness to permit microscopic examination of said tissue specimens, and placing at least one of said sections on a surface for inspection.

2. The method as in claim 1 wherein said matrix is paraffin.

3. The method as in claim 1 wherein said holder is a plastic drinking straw.

4. The method as in claim 1 further comprising depositing an antibody preparation on said section.

5. A method for testing immunohistochemical reactivity of a monoclonal antibody against multiple tissue samples simultaneously, comprising:

providing a plurality of tissue specimens, boring at least one core from each of said specimens, assembling and arranging said cores to obtain a plurality of cores of tissue specimens, arranged in concentric circles in a tubular holder, whereby said cores retain the same spatial relationship throughout the length of the holder fixing said plurality of assembled cores in position in said holder casing with a heat softened synthetic or natural binder matrix to encompass said holder and said cores with said matrix, cooling and removing said matrix from around said holder after solidification of said matrix, removing said holder casing from said cores, cutting at least one section from said cores in the matrix to obtain a thin section suitable for microscopic inspection of said tissue specimens, placing at least one of said sections on a surface for inspection, depositing an antibody preparation on said surface, and examining any sections so treated.

6. The method as in claim 5 wherein said matrix is paraffin.

7. The method as in claim 5 wherein said holder is a plastic drinking straw.

8. The method as in claim 5 wherein said holder is a paper casing.

* * * * *